(12) United States Patent
Choi et al.

(10) Patent No.: US 8,608,636 B2
(45) Date of Patent: Dec. 17, 2013

(54) VENTRICULAR ASSIST DEVICE CANNULA AND VENTRICULAR ASSIST DEVICE INCLUDING THE SAME

(75) Inventors: Sung Wook Choi, Chuncheon-si (KR); Byoung Goo Min, Goyang-si (KR)

(73) Assignee: Libraheart, Inc.V, Jeju-Si (KR)

( * ) Notice: Subject to any disclaimer, the term of this patent is extended or adjusted under 35 U.S.C. 154(b) by 0 days.

(21) Appl. No.: 13/286,631

(22) Filed: Nov. 1, 2011

(65) Prior Publication Data

US 2012/0310037 A1 Dec. 6, 2012

(30) Foreign Application Priority Data

Nov. 12, 2010 (KR) .......... 10-2010-0112662
Nov. 25, 2010 (KR) .......... 10-2010-0118306
Dec. 13, 2010 (KR) .......... 10-2010-0126867
Dec. 16, 2010 (KR) .......... 10-1010-0129026
Dec. 16, 2010 (KR) .......... 10-2010-0129036

(51) Int. Cl.
*A61N 1/362* (2006.01)
*A61N 1/00* (2006.01)

(52) U.S. Cl.
USPC .......... 600/17; 600/16; 607/5; 607/8

(58) Field of Classification Search
USPC ...................... 600/16–17; 607/5, 8
See application file for complete search history.

(56) References Cited

U.S. PATENT DOCUMENTS

| 4,925,443 | A | 5/1990 | Heilman | |
|---|---|---|---|---|
| 2005/0085683 | A1* | 4/2005 | Bolling et al. .......... | 600/16 |
| 2009/0209872 | A1* | 8/2009 | Pop .......... | 600/506 |

FOREIGN PATENT DOCUMENTS

| JP | 06-14961 B2 | 3/1994 |
|---|---|---|
| JP | 2006-508767 A | 3/2006 |
| JP | 2008-264512 A | 11/2008 |
| KR | 10-2010-0096474 A | 9/2010 |
| WO | 2004/052172 A3 | 6/2004 |

OTHER PUBLICATIONS

Yoo Seok Kim et al., "Development of a Pacemaker with Ventricular Assist Device for End-stage Heart Failure Patients", 2011 KSME Spring Conference—Biomedical Section, Apr. 29, 2011.
Yoo Seok Kim et al., "The Ventricular Assist Device with a Pacemaking Function for End Stage Heart Failure Patient's Survival Rate", 2011 IEEK Summer Conference, Jun. 22, 2011.
Mun-Soo Kim et al., "Measurement of cardiac valve opening time using impedance to cortrol for VAD", The Institute of Electronics Engineers of Korea, May 14, 2011.
Y.S. Kim et al., "Development of Pulsatile Left Ventricle Assist Device Compose with the Pacemaker function", The Korea Society of Medical & Biological Engineering, May 14, 2011.
S.M.Kang et al., "Conduit Ventricular Assist Device to Increase Survival Rate even if Function Stopped", The Korea Society of Medical & Biological Engineering, May 14, 2011.

(Continued)

*Primary Examiner* — Nicole F Lavert
(74) *Attorney, Agent, or Firm* — Lexyoume IP Meister, PLLC.

(57) ABSTRACT

Provided is a ventricular assist device cannula, and more particularly, a ventricular assist device cannula with electrodes. An exemplary embodiment of the present invention provides a ventricular assist device cannula with electrodes, including: a connecting tube connecting an incision of a body tissue and a ventricular assist device so that blood can flow; and electrodes connected with the connecting tube and contacting the incision of the body tissue to transfer an electric signal to the body tissue.

10 Claims, 18 Drawing Sheets

(56) References Cited

OTHER PUBLICATIONS

Y.S. Kim et al., "Development of Pulsatile Conduit Type Left Ventricular Assist Device Combined with the Internal Cardioverter Defibrillator", The Korea Society of Medical & Biological Engineering, Nov. 11, 2011.

Yoo Seok Kim et al., "Development of the Pacemaker with Ventricular Assist Device for End-stage Heart Failure Patients" Transactions of the KSME B, 2011, vol. 35 No. 11, pp. 1205-1211, Apr. 28, 2011.

Yoo Seok Kim, et al., "Development of Defibrillatior Using Apex Cannula Electrode of VAD", Proceedings of the KSME 2010 Fall Annual Meeting, Nov. 4, 2010, p. 331.

Yoo Seok Kim, et al., "Implantable Cardioverter Defibrillator Using Catheter Electrodes of Ventricula Assist Device", Journal of Vascular Biomedical Engineering, Nov. 2010, p. 53.

M.S. Kim, et al., "Impedance Mmeasurement for an Implanted Patient with Ventricular Assist Device", Journal of Vascular Biomedical Engineering, Nov. 2010, p. 57.

* cited by examiner

VENTRICULAR ASSIST DEVICE CANNULA AND VENTRICULAR ASSIST DEVICE INCLUDING THE SAME

CROSS-REFERENCE TO RELATED APPLICATION

This application claims priority to and the benefit of Korean Patent Application Nos. 10-2010-0112662, 10-2010-0118306, 10-2010-0126867, 10-2010-0129026, and 10-2010-0129036 filed in the Korean Intellectual Property Office on Nov. 12, 2010, Nov. 25, 2010, Dec. 13, 2010, Dec. 16, 2010, and Dec. 16, 2010, the entire contents of which are incorporated herein by reference.

BACKGROUND OF THE INVENTION (a) Field of the Invention

The present invention relates to a ventricular assist device cannula and a ventricular assist device including the same.

(b) Description of the Related Art

A ventricular assist device (VAD) is generally used in the case where an internal treatment has no effect on patients with heart failure or the heart failure is difficult to treat by open heart surgery. The ventricular assist device is operated so as to replace the function of a ventricle before imprinting a heart or used in order to induce recovery by reducing a load of the heart. The ventricular assist device generally has a structure which aspirates blood from an atrium or a ventricle by using a cannula and then ejects the blood to the aorta.

The ventricular assist device is classified into an implantable type ventricular assist device and an extracoporeal type ventricular assist device according to an implanted region and into a left ventricular assist device (LVAD), a right ventricular assist device (RVAD), and a biventricular assist device (Bi-VAD) according to an assisted heart region. The left ventricular assist device is mainly used. In addition, as another classifying method, the ventricular assist device may be classified into a pneumatic type and an electric type according to a difference in methods of supplying a power source. The electric type is sub-classified into an electrohydraulic type and an electromechanical type. In addition, the ventricular assist device may be classified into a pulsatile type and a nonpulsatile type according to the existence of pulsation when the blood is ejected according to a driving manner. In addition, an implantable biventricular assist device corresponds to a mechanical heart, but is differentiated from a totally implantable mechanical heart in which blood circulation is performed by only the mechanical heart after removing a natural heart.

Since a patient with a terminal heart disease using the ventricular assist device complexly shows problems such as the loss of a pumping function of the heart, arrhythmia or ventricular fibrillation, and ischemia, it is difficult to expect a significant improvement of the survival rate of the patient by using only the ventricular assist device.

For example, even though the patient with the terminal heart disease uses the ventricular assist device, the patient may die from interruption of pulsation of the heart. Therefore, the survival rate needs to be increased by using a defibrillator together. Further, it is almost impossible to anticipate the pulsation timing of the heart of a patient with arrhythmia, a possibility that simultaneous pulsation which may impose a burden on the heart may occur is very high. Therefore, an artificial pacemaker capable of adjusting the pulsation timing of the heart needs to be used in conjunction with the ventricular assist device.

However, since a separate electrode for applying an electric stimulus to the heart has to be transplanted in order to mount the defibrillator and the artificial pacemaker, respectively, an additional operation and an in-vivo volume of the patient are required.

Meanwhile, when a separate external defibrillator is used, malfunction and damage of the ventricular assist device may occur.

Meanwhile, the existing ventricular assist device can measure or estimate its own blood ejection amount, but since the existing ventricular assist device cannot find a cardiac ejection amount of a patient and a total blood circulation amount, the existing ventricular assist device cannot perform optimal control according to a physiological condition of the patient. When the ventricular assist device is used, an optimal amount of blood flow which the ventricular assist device will supply depending on the physiological condition of the patient is changed. It was difficult for the existing ventricular assist device to be equipped with an appropriate measurement device for expecting physiological variation of the patient. If a blood flow supply amount of the ventricular assist device is excessively large, arteries or heart tissues around an inlet catheter may be narrowed or damaged and if the blood flow supply amount thereof is excessively small, an effect of assisting the heart is reduced. Further, when the ventricular assist device co-pulsates while the heart pulsates, a large load is applied to a heart muscle to damage the heart muscle. Therefore, a measurement technology which can be easily applied to the existing ventricular assist device simultaneously when measuring the cardiac output and a cardiac ejection timing of the patient needs to be developed.

Meanwhile, the artificial pacemaker which normally pulsates the heart by using an electric stimulus principle is primarily used for a patient who has a pulse slower than a normal pulse or is under a risk of an expected death. The artificial pacemaker is constituted by two parts of a pace generator and an electrode line. Between them, the pace generator is a metallic case including an electronic circuit controlling the electric stimulus and a battery and the electrode line serves to pulsate the heart by transferring electricity or send an electrical signal generated from the heart to the pace generator. The artificial pacemaker is divided into a temporary type and a permanent type. In the temporary type, the power supply is provided outside the body and is used for a patient who requires pacemaking for several days. The permanent type is used for a patient who requires peacemaking for a long period of time with a power supply thereof buried in the body. The pace generator is buried below a skin of an upper part of a chest and the electrode line is inserted into the blood vessel to be connected to the inside of the heart. The electrode line may be fixed to the heart muscle. The artificial pacemaker has a light weight of 20 to 30 g and also has a small size. The life-span of the battery is continued for 7 to 13 years. Further, there is also provided a fully automatic type which has an output of the power supply and pulsation rate which can be controlled outside the body and functions similar to a normal heart so as to allow the patient to act similarly to a normal person.

Actually, it is almost impossible to anticipate a timing of the heart beat of the heart of the patent with arrhythmia. Accordingly, when only the ventricular assist device is used, a possibility that simultaneous pulsation which may impose the large burden on the heart will occur is very high.

The above information disclosed in this Background section is only for enhancement of understanding of the background of the invention and therefore it may contain information that does not form the prior art that is already known in this country to a person of ordinary skill in the art.

SUMMARY OF THE INVENTION

The present invention has been made in an effort to provide a ventricular assist device cannula with electrodes having advantages of transferring an electric stimulus to a heart and a blood vessel by a defibrillator and an artificial pacemaker, and the like so as to easily use devices such as the defibrillator, the artificial pacemaker, and the like together with the ventricular assist device.

Further, the present invention has been made in an effort to provide a ventricular assist device cannula with electrodes having another advantage of increasing patient's survival rate and minimizing malfunction and damaging causes of the device by developing a fusion device for minimizing an influence on each other while the ventricular assist device and the defibrillator operate simultaneously.

In addition, the present invention has been made in an effort to provide a ventricular assist device having another advantage of easily measuring a cardiac output and an output timing by installing electrodes in a cannula used in the ventricular assist device and measuring impedance between a heart and aorta.

Moreover, the present invention has been made in an effort to provide a ventricular assist device including an artificial pacemaker having advantages of preventing the ventricular assist device from being co-pulsated with the heart by controlling a timing and frequency of a heart beat using the artificial pacemaker.

An exemplary embodiment of the present invention provides a ventricular assist device cannula with electrodes, including: a connecting tube connecting an incision of a body tissue and a ventricular assist device so that blood can flow; and electrodes connected with the connecting tube and contacting the incision of the body tissue to transfer an electric signal to the body tissue.

The electrode may be a conductive sheet attached to the surface of the connecting tube.

The electrode may be a hollow electrode which has a hollow space into which the connecting tube is inserted at the inside thereof and is contacted to the incision of the body tissue at the outside thereof. A receiving groove receiving the incision of the body tissue may be formed at an outer circumference of the hollow electrode.

The electrode may be a connector electrode which has hollow space where the blood can flow at the inside thereof and includes a body part closely contacted to the incision of the body tissue and inserted into the body tissue and a fixing part extending from the body part and inserted and fixed to the connecting tube at the outside thereof. A receiving groove receiving the incision of the body tissue may be formed at an outer circumference of the body part.

The electrode may have a hollow space where the blood can flow at the inside thereof and includes a body part closely contacted to the incision of the body tissue and fixing parts extending from the body part to the upstream and the downstream, respectively, at the outside thereof, and the connecting tube may include a first connecting tube having one end connected to the fixing part and the other end inserted into the body tissue and a second connecting tube having one end connected to the fixing part and the other end connected to the ventricular assist device. A receiving groove receiving the incision of the body tissue may be formed at an outer circumference of the body part.

Another exemplary embodiment of the present invention provides a ventricular assist device including a defibrillator in the ventricular assist device including a blood pump pumping the blood, the device including: at least a pair of conduits including a connecting tube connecting an incision of a body tissue and the blood pump so that the blood can flow and electrodes connected with the connecting tube and contacting the incision of the body tissue to transfer an electric signal to the body tissue; a detecting device detecting an abnormality of heart beat or not; a defibrillator applying an electric stimulus to the heart by applying a defibrillation pulse to the electrode; and a control device receiving a signal from the detecting device to control the blood pump and the defibrillator.

The detecting device may include a pressure sensor measuring an inlet pressure of the conduit.

The detecting device may include an impedance measuring device measuring impedance between the electrodes.

The control device may operate a protection mode blocking a power supply and input and output signals of the ventricular assist device when defibrillation energy for applying a defibrillation pulse is charged in the defibrillator. The control device may include an external alarm device sounding the alarm when ventricular fibrillation and a cardiac arrest are detected through the detecting device.

Yet another exemplary embodiment of the present invention provides a ventricular assist device including an impedance measuring device in the ventricular assist device including a first conduit and a second conduit where blood flows and a blood pump pumping the blood, the device including: a first conduit including a connecting tube connecting an incision of a first body tissue and the blood pump so that the blood can flow and a first electrode connected with the connecting tube and contacting the incision of the first body tissue to transfer an electric signal to the first body tissue; a second electrode spaced apart from the first electrode with the first body tissue interposed therebetween so as to measure impedance due to the blood flow in the first body tissue connected to the first conduit; an impedance measuring device measuring impedance between the first electrode and the second electrode; and a control device receiving a signal from the impedance measuring device to control operation of the blood pump.

Still another exemplary embodiment of the present invention provides a ventricular assist device including an artificial pacemaker in the ventricular assist device including a blood pump pumping the blood, the device including: at least a pair of conduits including a connecting tube connecting an incision of a body tissue and the blood pump so that the blood can flow and electrodes connected with the connecting tube and contacting the incision of the body tissue to transfer an electric signal to the body tissue; a detecting device detecting a cardiac signal of a patient; an artificial pacemaker applying an electric stimulus to the heart through the electrode; and a control device receiving a signal from the detecting device to control the blood pump and the artificial pacemaker.

The detecting device may include a pressure sensor measuring an inlet pressure of the conduit.

The detecting device may include an impedance measuring device measuring impedance between the electrodes.

The control device may compare heart rate with pulsation rate of the blood pump, and if the heart rate is smaller than the pulsation rate of the blood pump, the heart rate may be equal to the pulsation rate of the blood pump by controlling the artificial pacemaker, and if the heart rate is X to X+1 times (X is a natural number of 1 or more) larger than the pulsation rate of the blood pump, the heart rate may be equal to be X+1 times of the pulsation rate of the blood pump by controlling the artificial pacemaker.

The control device may control a blood pump output using a cardiac output measured in the detecting device as a parameter.

According to the exemplary embodiments of the present invention, the ventricular assist device cannula with electrodes has effects as follows.

First, a bio-signal of a patient wearing the ventricular assist device through the electrode attached to the conduit can be easily measured without a separate electrode implant and an electric stimulus can also be measured.

Second, since the electric stimulus can be directly applied to a cardiac muscle, it is possible to improve stability and efficiency of an electric treatment such as a cardiac pacemaking, a ventricular defibrillation, and the like of the patient wearing the ventricular assist device.

According to the exemplary embodiments of the present invention, it is possible to provide an efficient defibrillation method for restoring a heart function against fatal arrhythmia which may occur during a use of the ventricular assist device. Further, it is possible to minimize possibilities of malfunction and damage of the ventricular assist device which may occur by an operation of a separate defibrillator. In addition, a fast and efficient defibrillation can be performed even by a small electric stimulus as compared with a general defibrillation method by applying a direct electric stimulus to a Purkinje fiber of a heart muscle.

According to the exemplary embodiments of the present invention, the ventricular assist device including a measuring device of a cardiac output and a cardiac output timing has effects as follows.

First, since a blood flow of a patient and an output timing of blood are expected by measuring impedance, it is possible to perform an optimal contral suitable for a physiological condition of the patient. That is, when the circulation of the entire blood flow is reduced, the blood flow speed of the ventricular assist device decreases, such that it is possible to prevent the blood vessel from being contracted or damaged due to an excessive inflow of the blood flow and minimize a load applied to the heart of the patient due to a simultaneous beat by preventing the blood ejection of the ventricular assist device in the heart ejection.

Second, it is possible to verify an open or close of valves by measuring impedance of a current path to be connected to a blood vessel, an aortic valve, and a heart of the patient.

Third, it is possible to measure and monitor a heart beat state and a motion state of valves of the patient for a long time without a separate expert and detect a dangerous factor in real time.

According to the exemplary embodiments of the present invention, since the ventricular assist device can control a timing of the heart beat by using an artificial pacemaker, it is possible to prevent fatal arrhythmia and simultaneous pulsation generated during a use of the ventricular assist device. Further, a fast and efficient cardiac pacemaking can be performed even by a small electric stimulus as compared with a general defibrillation method by applying a direct electric stimulus to a Purkinje fiber of a heart muscle.

DETAILED DESCRIPTION OF THE EMBODIMENTS

Hereinafter, exemplary embodiments of a ventricular assist device cannula with electrodes according to the present invention will be described in detail with reference to the accompanying drawings.

Figure 1:
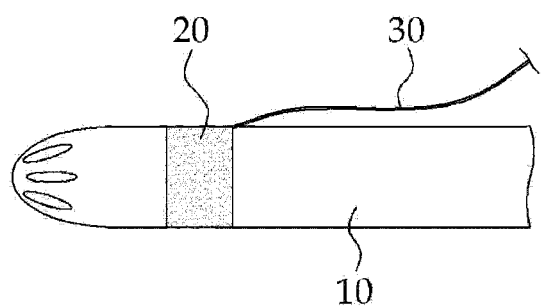
FIG. 1 is a side view of a ventricular assist device cannula with electrodes according to a first exemplary embodiment of the present invention.
Figure 2:
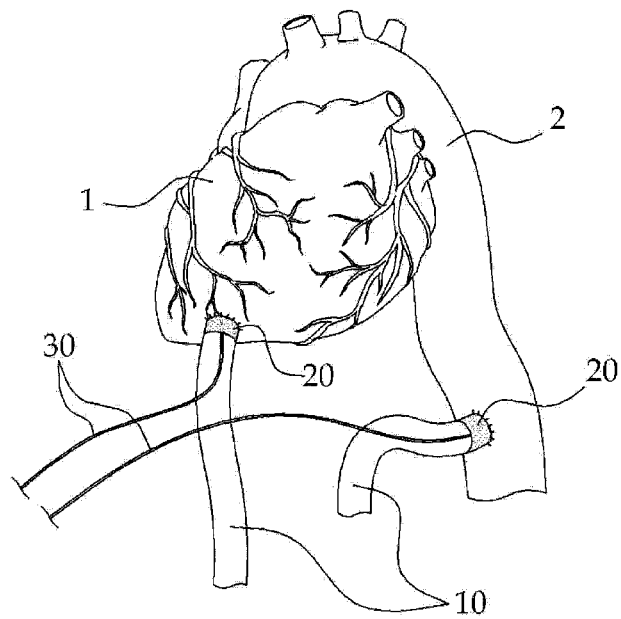
FIG. 2 is a perspective view illustrating a state where the ventricular assist device cannula with electrodes shown in FIG. 1 is mounted on a human body.

FIG. 1 is a side view of a ventricular assist device cannula with electrodes according to a first exemplary embodiment of the present invention and FIG. 2 is a perspective view illustrating a state where the ventricular assist device cannula with electrodes shown in FIG. 1 is mounted on a human body.

Referring to FIGS. 1 and 2, a ventricular assist device cannula with electrodes according to a first exemplary embodiment of the present invention includes a connecting tube 10 and a conductive sheet 20 attached to the surface of the connecting tube 10.

The connecting tube 10 means a hollow elongated pipe so that blood can flow. The connecting tube 10 acts to connect the ventricular assist device with ventricles 1 and arteries 2 and transfer the blood of the ventricles 1 to the arteries 2. The connecting tube 10 may be made of a flexible material, but is more preferably made of an elastic material allowing contraction and expansion in order to serve as an apico arotic conduit (AAC) reducing a load of the heart when being not used as the ventricular assist device. In addition, the connecting tube 10 is preferably made of biomacromolecules having excellent blood compatibility and durability, for example, polyurethane for medical use and the like.

The conductive sheet 20 is attached to the surface of the connecting tube 10 and connected with a defibrillator, an artificial pacemaker, and the like through wires 30. The conductive sheet 20 is made of Ag/AgCl, platinum (Pt), gold (Au), or other electrode materials. The conductive sheet 20 is attached to a position contacting a cross-section of an incision, when the connecting tube 10 is inserted to the ventricles 1 and the arteries 2 through the incision of a body tissue such as the ventricles 1 and the arteries 2. Accordingly, an electric signal transferred through the conductive sheet 20 may be directly transferred to muscle cells or conductive fibers (purkinje fibers) of the heart, such that there is a merit that an electric stimulus can be efficiently applied to the whole heart even through small electric energy.

Figure 3:
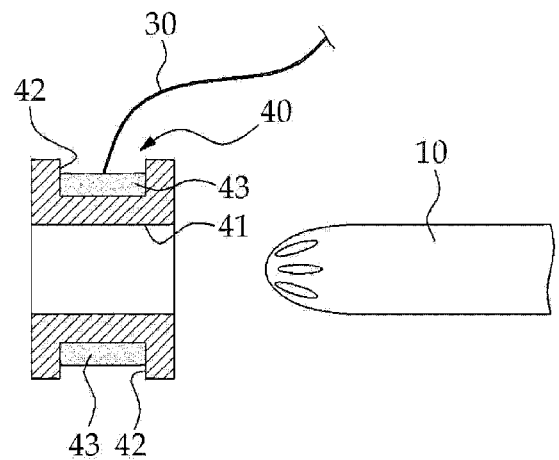
FIG. 3 is a partial cross-sectional view of a ventricular assist device cannula with electrodes according to a second exemplary embodiment of the present invention.

FIG. 3 is a partial cross-sectional view of a ventricular assist device cannula with electrodes according to a second exemplary embodiment of the present invention. Referring to FIG. 3, the ventricular assist device cannula with electrodes according to the second exemplary embodiment of the present invention includes a connecting tube 10 and a hollow electrode 40. Since the connecting tube 10 is the same as that of the first exemplary embodiment, the description thereof is omitted and only the hollow electrode 40 will be described.

The hollow electrode 40 with a cylindrical shape has a hollow space 41 into which the internal connecting tube 10 can be inserted. A receiving groove 42 which can receive the incision of the body tissue is formed around the hollow electrode 40. When the hollow electrode 40 is inserted through the incision of the body tissue, the incision of the body tissue is fitted into the receiving groove 42. The connecting tube 10 is inserted inside the body tissue through the hollow space 41 of the hollow electrode 40. A conductive layer 43 made of an electrode material such as Ag/AgCl, platinum (Pt), gold (Au), or the like is formed inside the receiving groove 42 of the hollow electrode 40 and connected with a defibrillator, an artificial pacemaker, and the like through the wires 30. Meanwhile, the overall hollow electrode may be made of the electrode material without forming a separate conductive layer 43.

Figure 4:
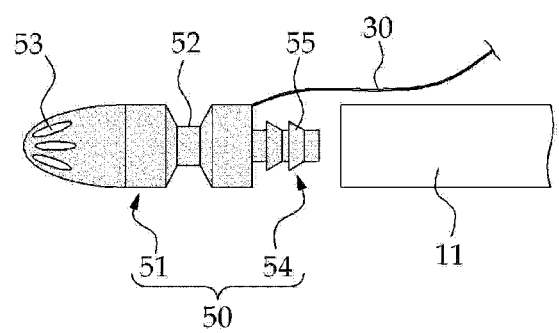
FIG. 4 is an exploded side view of a ventricular assist device cannula with electrodes according to a third exemplary embodiment of the present invention.

FIG. 4 is an exploded side view of a ventricular assist device cannula with electrodes according to a third exemplary embodiment of the present invention. Referring to FIG. 4, the ventricular assist device cannula with electrodes according to the third exemplary embodiment of the present invention includes a connecting tube 11 and an electrode 50 including a body part 51 and a fixing part 54.

The body part 51 includes a hollow space (not shown) in which blood can flow and a receiving groove 52 for receiving an incision of the body tissue around the body part 51 like the second exemplary embodiment. In FIG. 4, through-holes 53 through which the blood passes are formed at a left end of the body part 51 and the fixing part 54 extending from the body part 51 is formed at a right end of the body part 51.

The fixing part 54 is inserted into the connecting tube 11 to serve to connect the electrode 50 and the connecting tube 11 and includes a protrusion 55 for preventing a connecting part from being easily separated.

Figure 5:
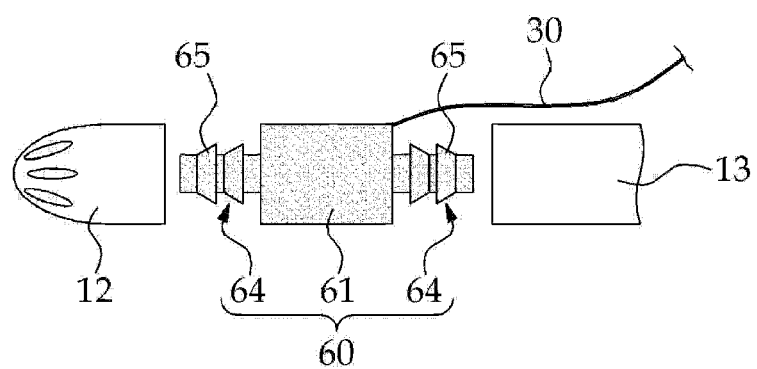
FIG. 5 is an exploded side view of a ventricular assist device cannula with electrodes according to a fourth exemplary embodiment of the present invention.

FIG. 5 is an exploded side view of a ventricular assist device cannula with electrodes according to a fourth exemplary embodiment of the present invention. Referring to FIG. 5, the ventricular assist device cannula with electrodes according to the fourth exemplary embodiment of the present invention includes a connecting tube divided into a first connecting tube 12 and a second connecting tube 13, and an electrode 60 including a body part 61 and fixing parts 64.

A hollow space (not shown) in which blood can flow is formed inside the body part 61 and an outer surface of the body part 61 is closely contacted to the incision of the body tissue.

The fixing parts 64 extend to a left side and a right side from the body part 61, respectively and include protrusions 65 for preventing the fixing parts 64 from being easily separated from the connecting tubes 12 and 13.

One end of the first connecting tube 12 is connected to the left fixing part 64 and the other end thereof is inserted inside the body tissue, and one end of the second connecting tube 13 is connected to the right fixing part 64 and the other end thereof is connected to the ventricular assist device (not shown).

Figure 6:
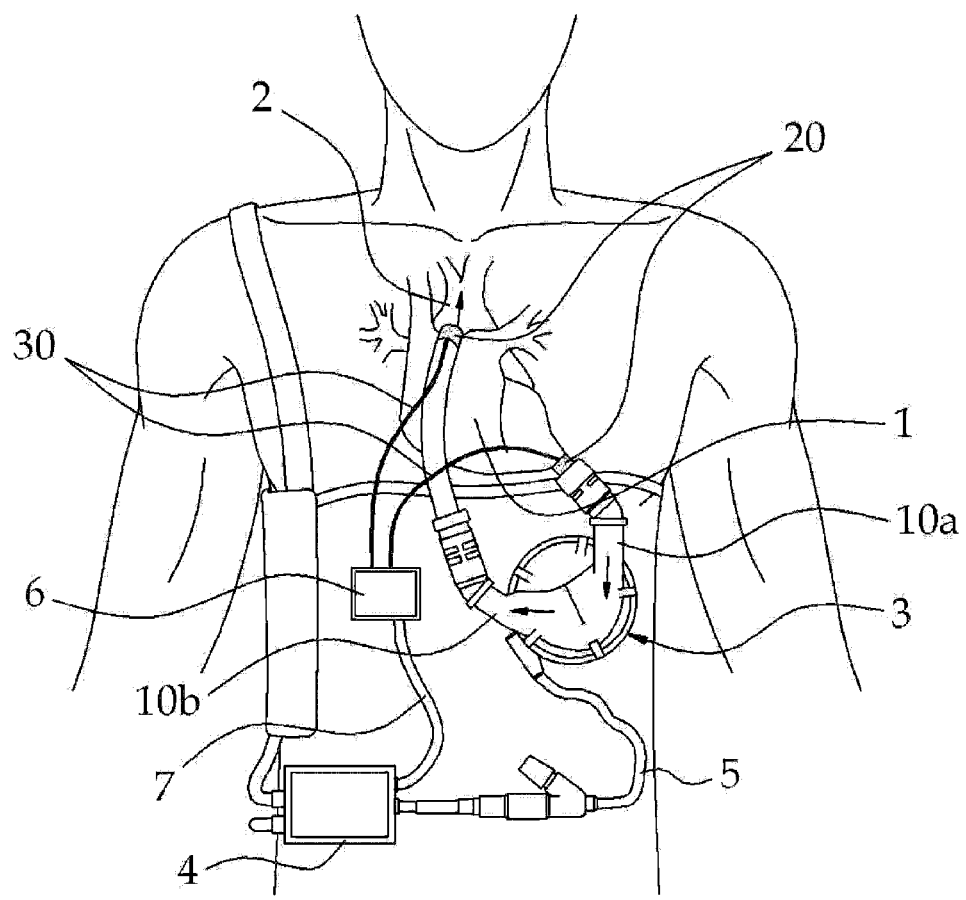
FIG. 6 is a schematic configuration diagram illustrating a state where a ventricular assist device including the ventricular assist device cannula with electrodes shown in FIG. 1 and a defibrillator are mounted on a human body.

FIG. 6 is a schematic configuration diagram illustrating a state where a ventricular assist device including the ventricular assist device cannula with electrodes shown in FIG. 1 and a defibrillator are mounted on a human body.

Referring to FIG. 6, the ventricular assist device includes an inflow connecting tube 10a connected to a cardiac apex 1 of a left ventricle, an outflow connecting tube 10b connected to aorta 2, and a blood pump 3 connected with the inflow connecting tube 10a and the outflow connecting tube 10b. A one-way valve (not shown) permitting only one direction flow of blood is installed at the inflow connecting tube 10a and the outflow connecting tube 10b. A battery and a control device 4 are installed outside the body and connected to the blood pump 3 through a wire 5 by passing through skin. Ejection of the blood is controlled by the control device 4 and the battery supplies power to the control device 4 and an electric motor.

A defibrillator 6 is connected to electrodes 20 of the inflow connecting tube 10a and the outflow connecting tube 10b through the wire 30 and connected with the control device 4 by a wire 7 passing through the skin. Since the electrodes 20 are attached to the inflow connecting tube 10a and the outflow connecting tube 10b, there is no need to implant a separate wire into a heart or arteries. Although not shown, an electrocardiograph for checking whether ventricular fibrillation occurs is connected with the control device 4.

Hereinafter, operations of the ventricular assist device and the defibrillator will be described shown in FIG. 6. When the blood pump 3 operates in accordance with a signal of the control device 4, the blood flows from the left ventricle 1 to the blood pump 3 through the inflow connecting tube 10a. The blood flowing into the blood pump 3 is supplied to the aorta 2 through the outflow connecting tube 10b. In this case, the electrocardiograph (not shown) checks a state of the heart continuously to transfer the signal to the control device 4. When the ventricular fibrillation is checked by the electrocardiograph, the control device 4 stops operation of the blood pump 3 and operates the defibrillator 6. The defibrillator 6 directly applies the electric stimulus to muscles of the ventricle 1 and the blood 2 through the electrodes 20 installed at the inflow connecting tube 10a and the outflow connecting tube 10b. If it is checked that a heart beat is restored in a normal state by the electric stimulus, the control device 4 operates the blood pump 3 again.

Figure 7:
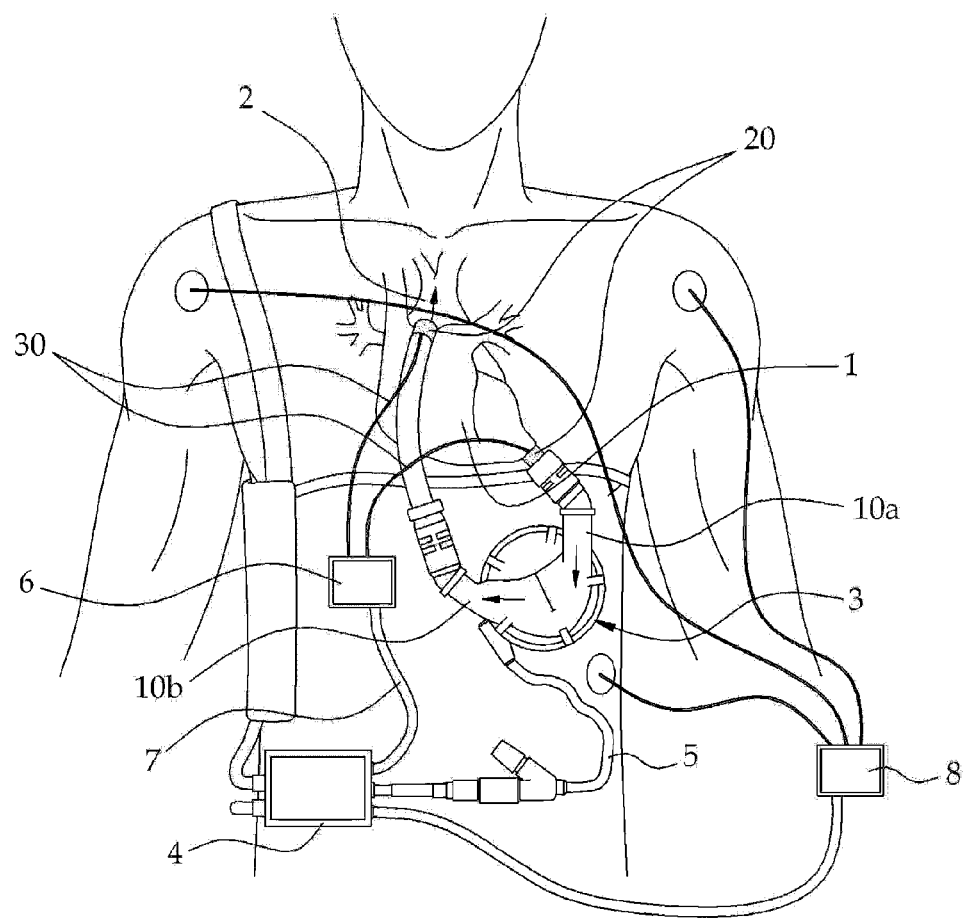
FIG. 7 is a conceptual diagram of a ventricular assist device including a defibrillator according to an exemplary embodiment of the present invention.
Figure 8:
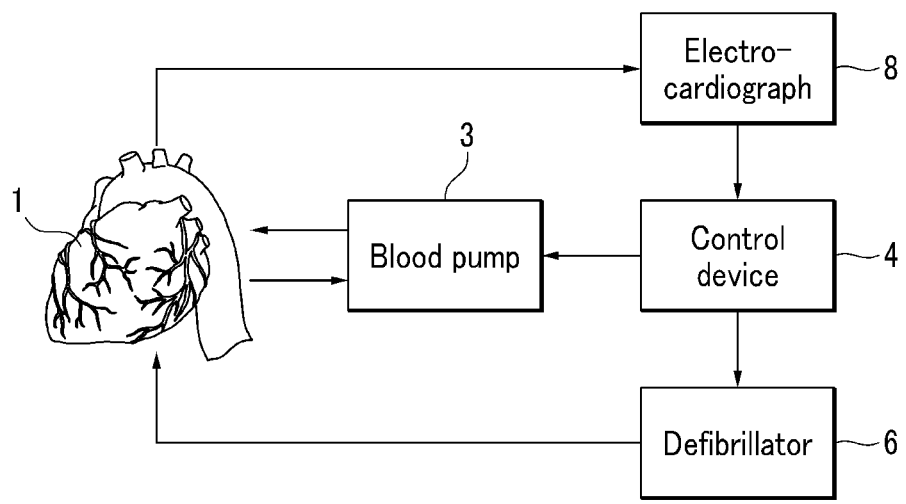
FIG. 8 is a block diagram of the ventricular assist device shown in FIG. 7.

FIG. 7 is a conceptual diagram of a ventricular assist device including a defibrillator according to an exemplary embodiment of the present invention and FIG. 8 is a block diagram of the ventricular assist device shown in FIG. 7.

Referring to FIGS. 7 and 8, like a general ventricular assist device, a ventricular assist device including a defibrillator according to an exemplary embodiment of the present invention includes inflow conduits 10a and 20 into which the blood in a ventricle 1 flows while being connected to the ventricle 1, a blood pump 3 connected to the inflow conduits 10a and 20 and pumping the blood, and outflow conduits 10b and 20 connecting the blood pump 3 and arteries 2 to transfer the blood ejected from the blood pump 3 to the arteries 2. The inflow conduits and the outflow conduits are hollow elongated pipes so that the blood can flow. The inflow conduits and the outflow conduits may be the ventricular assist device cannula shown in FIGS. 1 to 6.

The blood pump 3 may be classified into a pneumatic type and an electric type. The electric type is subdivided into an electrohydraulic type and an electromechanical type. The blood pump 3 stores the blood flowing from the inflow connecting tube 10a and includes a blood bag flowing out to the outflow connecting tube 10b, air allowing the blood to flow by expanding and compressing the blood bag, and an electric device. Since the blood pump 3 uses a known device, the detailed description thereof is omitted.

Referring to FIGS. 7 and 8, the ventricular assist device including the defibrillator according to the exemplary embodiment of the present invention further includes a detecting device 8 detecting abnormality or normality in the heart beat, a defibrillator 6 applying a defibrillation pulse to the electrodes 20 of the conduits to apply the electric stimulus to the heart, and a control device 4 controlling the blood pump 3 and the defibrillator 6 by receiving the signal from the detecting device 8.

The detecting device 8 includes an electrocardiograph 8. The electrocardiogram records active current according to contraction of the heart in a curve line and is abbreviated to ECG or EKG. Since excitement of the heart muscle is generated from venous sinus to proceed in atrium and ventricle directions, when the excitement is induced to the electrocardiograph in any two points, the active current of the heart is drawn as a graph. As described above, the electrocardiogram is acquired. The abnormality or normality in the heart may be checked through the electrocardiogram. The detecting device 8 transmits measured data to the control device 4.

The defibrillator 6 includes a high voltage generating part for applying an electric impact and a high voltage switching part for discharging current generated from the high voltage generating part to a human body. The defibrillator 6 is implanted in a chest with being not seen at the outside or implanted together with being included in the control device 4. Since the defibrillator 6 uses a known device, the detailed description thereof is omitted.

The control device 4 includes a microcontroller which processes a signal measured through the detecting device 8 and determines the electric impact or not and an electric impact amount. The microcontroller controls the high voltage generating part of the defibrillator 6. In addition, the microcontroller controls the blood pump 3. Further, the control device 4 further includes an external alarm device (not shown) sounding the alarm when the ventricular fibrillation is checked.

Figure 9:
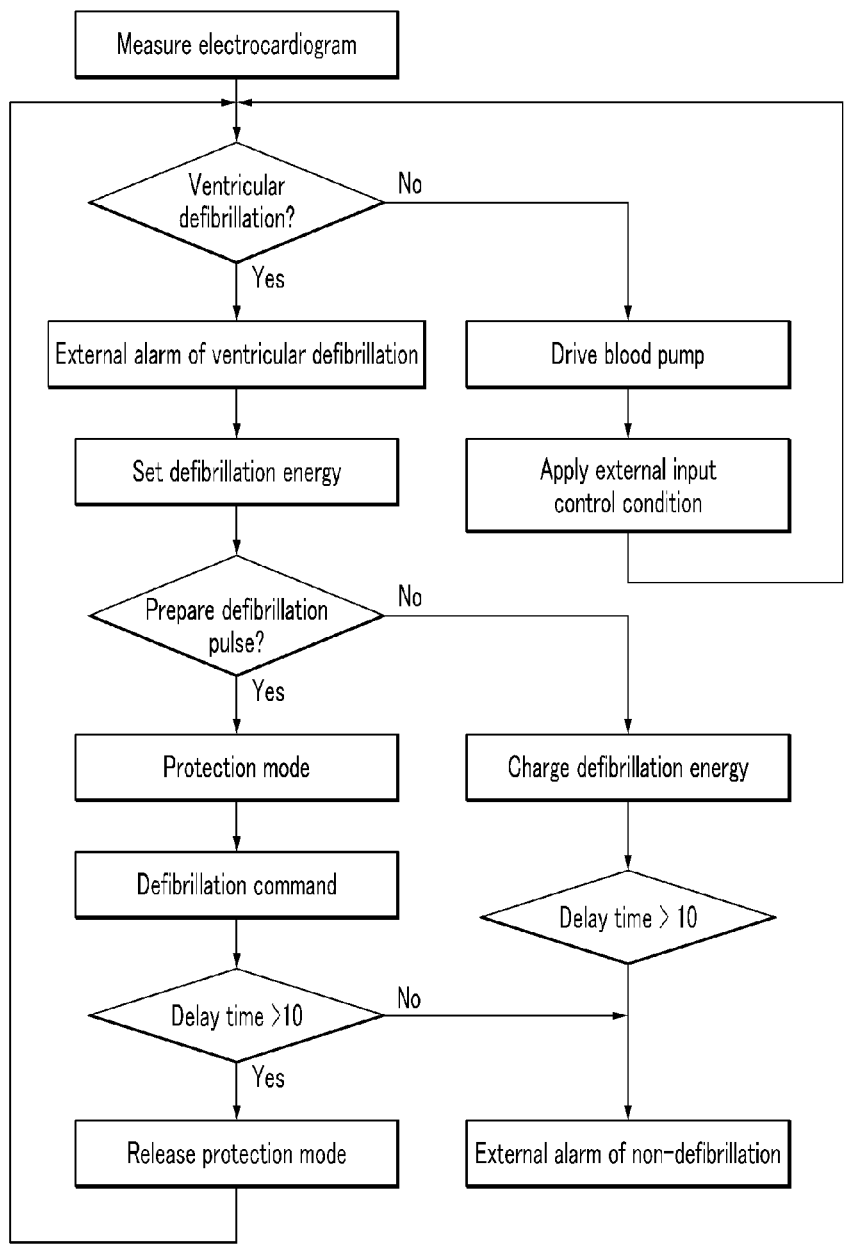
FIG. 9 is a flowchart illustrating operational steps of the ventricular assist device shown in FIG. 7.

FIG. 9 is a flowchart illustrating operational steps of the ventricular assist device shown in FIG. 7.

Referring to FIG. 9, operational steps of a ventricular assist device including a defibrillator according to an exemplary embodiment of the present invention start from measuring a cardiac state through a detecting device. If the measured signal is processed in a control device and there is no abnormality, a driving signal is transferred to a blood pump to drive the blood pump. If ventricular fibrillation is detected, an external alarm is sounded and an electric impact amount is determined to set defibrillation energy. When preparation for a defibrillation pulse is completed by charging the defibrillation energy, damage of the blood pump due to the defibrillation pulse is prevented by blocking a power supply for operation of the blood pump and entering a protection mode blocking input and output signals. If the ventricular fibrillation is removed by checking the defibrillation, the protection mode is released and the blood pump is operated again and if the defibrillation is failed, an inability alarm of the defibrillation is sounded.

Meanwhile, the detecting device 8 is described as a generally used electrocardiograph 8, but the detecting device 8 may use a pressure sensor installed at an inlet of the inflow conduit 10a. If the ventricular fibrillation occurs, each portion of the ventricle is disorderedly and irregularly contracted and flowability of blood flowing in through the inlet of the inflow conduit 10a becomes irregular. As a result, when the flowability is measured through the pressure sensor, the ventricular fibrillation or not may be checked. In addition, if a cardiac arrest occurs, the blood flowing into the inflow conduit 10a decreases and a pressure drops, such that the cardiac arrest or not may be checked. Further, as a method of measuring impedance between the electrodes of the inflow conduit and the outflow conduit, a detecting device measuring a cardiac abnormality such as the ventricular fibrillation, the cardiac arrest, and the like may be used. Since impedance between the electrodes 20 of the inflow conduit and the outflow conduit is changed according to a blood flow between the ventricle and the aorta, the cardiac abnormality or normality may be detected by measuring the impedance.

Figure 10:
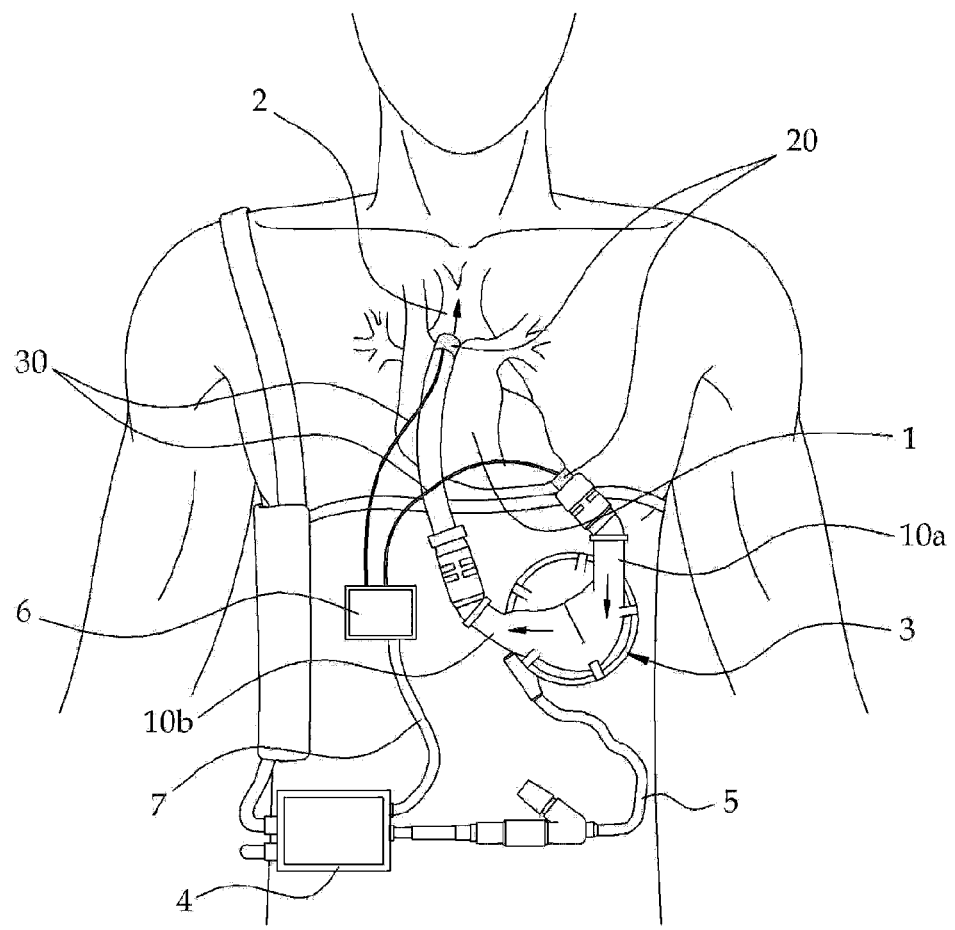
FIG. 10 is a conceptual diagram of a ventricular assist device including an impedance measuring device according to an exemplary embodiment of the present invention

FIG. 10 is a conceptual diagram of a ventricular assist device including an impedance measuring device according to an exemplary embodiment of the present invention.

Referring to FIG. 10, like a general ventricular assist device, a ventricular assist device including an impedance measuring device according to an exemplary embodiment of the present invention includes inflow conduits 10a and 20 into which the blood in a ventricle 1 flows while being connected to the ventricle 1, a blood pump 3 connected to the inflow conduits 10a and 20 and pumping the blood, and outflow conduits 10b and 20 connecting the blood pump 3 and arteries 2 to transfer the blood ejected from the blood pump 3 to the arteries 2. The inflow conduits and the outflow conduits are hollow elongated pipes so that the blood can flow. The inflow conduits and the outflow conduits may be the ventricular assist device cannula shown in FIGS. 1 to 6.

The blood pump 3 may be classified into a pneumatic type and an electric type. The electric type is subdivided into an electrohydraulic type and an electromechanical type. The blood pump 3 stores the blood flowing from the inflow connecting tube 10a and includes a blood bag flowing out to the outflow connecting tube 10b, air allowing the blood to flow by expanding and compressing the blood bag, and an electric device. Since the blood pump 3 uses a known device, the detailed description thereof is omitted.

Referring to FIG. 10, the ventricular assist device including an impedance measuring device according to the exemplary embodiment of the present invention further includes an impedance measuring device 6 and a control device 4 controlling the blood pump 3 by receiving a signal from the impedance measuring device 6.

The impedance measuring device 6 is connected to electrodes 20 through a wire 30. The impedance measuring device 6 includes a power supply device capable of applying high-frequency AC current. The high-frequency AC current is generated from the power supply device and the AC current is applied to the heart through the electrodes. When high-frequency current (30 kHz, 0.2 mA) having a sine waveform was applied between the heart and the blood vessel of a patient using the ventricular assist device, it was verified that the current has no influence on a nerve, muscle, or heart tissue. As the high-frequency current generated from the power supply device passes the heart and the blood vessel through the electrodes, high-frequency voltage is generated in proportion to magnitudes of impedances of the heart and the blood vessel. The impedance measuring device measures variation in an impedance value by measuring and recording the high-frequency voltage generated by the change of the impedance due to the heart beat.

Figure 11:
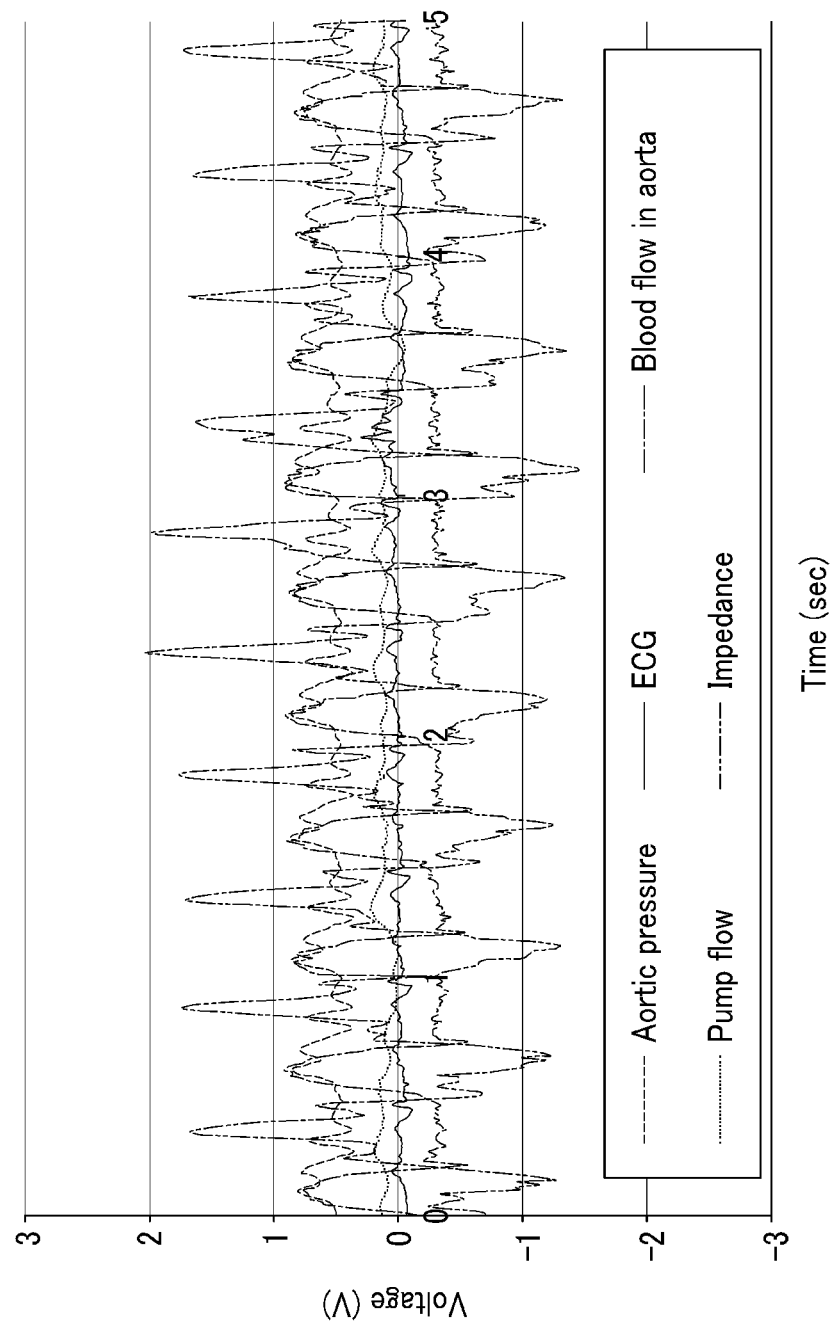
FIGS. 11 to 13 are diagrams illustrating variations in blood flow in aorta, arterial pressure, ECG, and impedance values when a stroke volume of the ventricular assist device is 0.5, 1.0, and 1.5 L/min.
Figure 12:
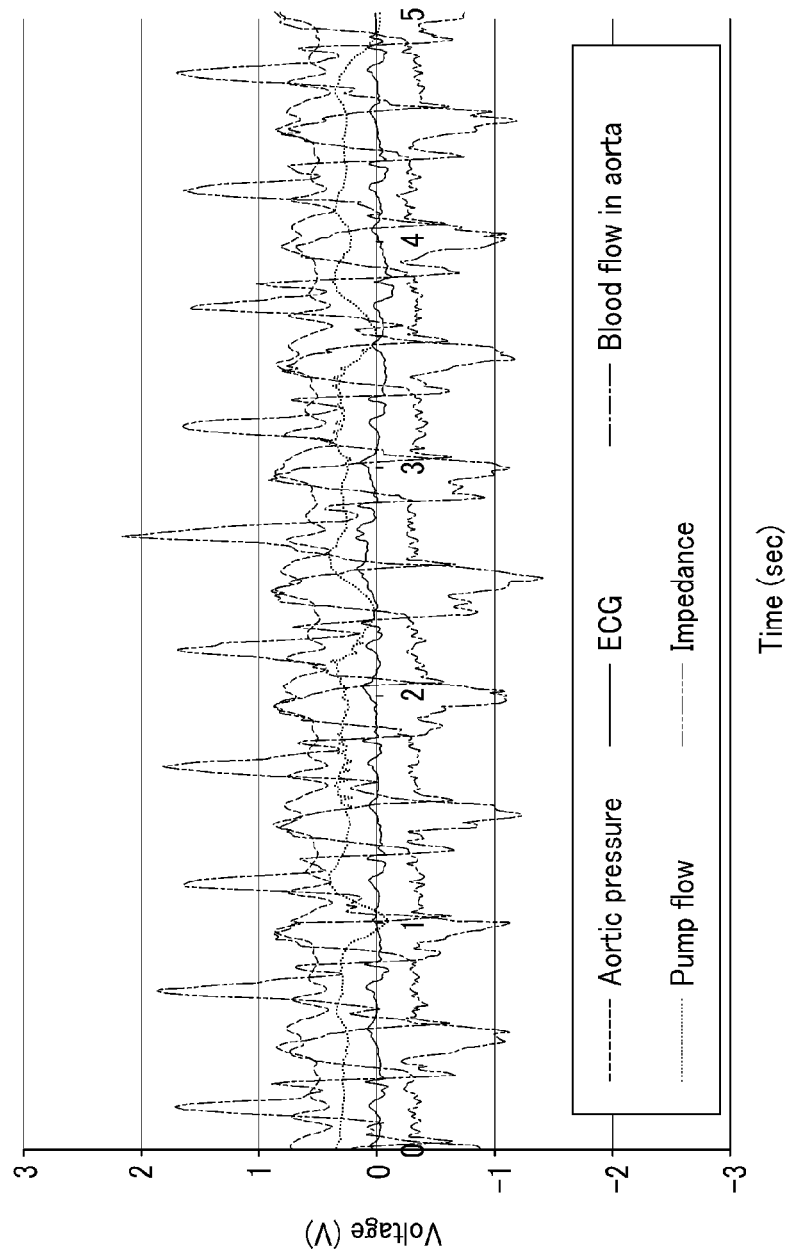
Figure 13:
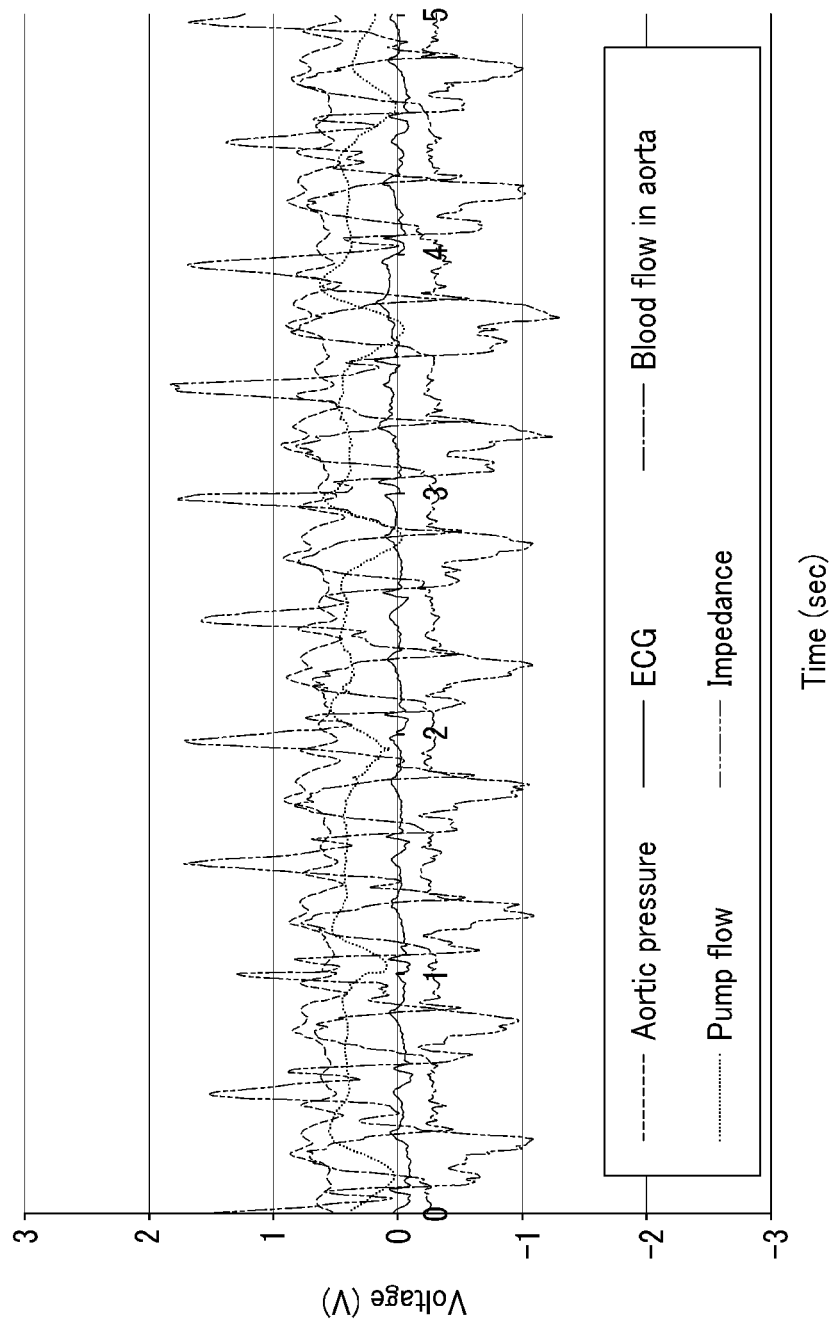

FIGS. 11 to 13 are diagrams illustrating variations in blood flow in aorta, arterial pressure, ECG, and impedance values when a stroke volume of the ventricular assist device is 0.5, 1.0, and 1.5 L/min. In an animal test using a pig of 40 Kg, the variations were measured by inserting an inflow conduit and an outflow conduit where electrodes are attached to a depth of a left ventricle and aorta. The variation in the blood flow in aorta was measured by using an ultrasonic flowmeter installed at an aortic arch.

As shown in FIGS. 11 to 13, the impedance value was changed according to open and close of cardiac valves, blood flow in ventricles, and blood flow in aorta. The open and close of the cardiac valves was verified through the aortic pressure. When the heart was contracted and the aortic valves opened, the impedance had a minimum value and when the arterial pressure was most low with the cardiac valves opened, the impedance had a maximum value. The impedance was increased and decreased when the cardiac valves opened and closed and particularly, inflection points were generated during the change of the impedance by the motion of the valves.

Figure 14:
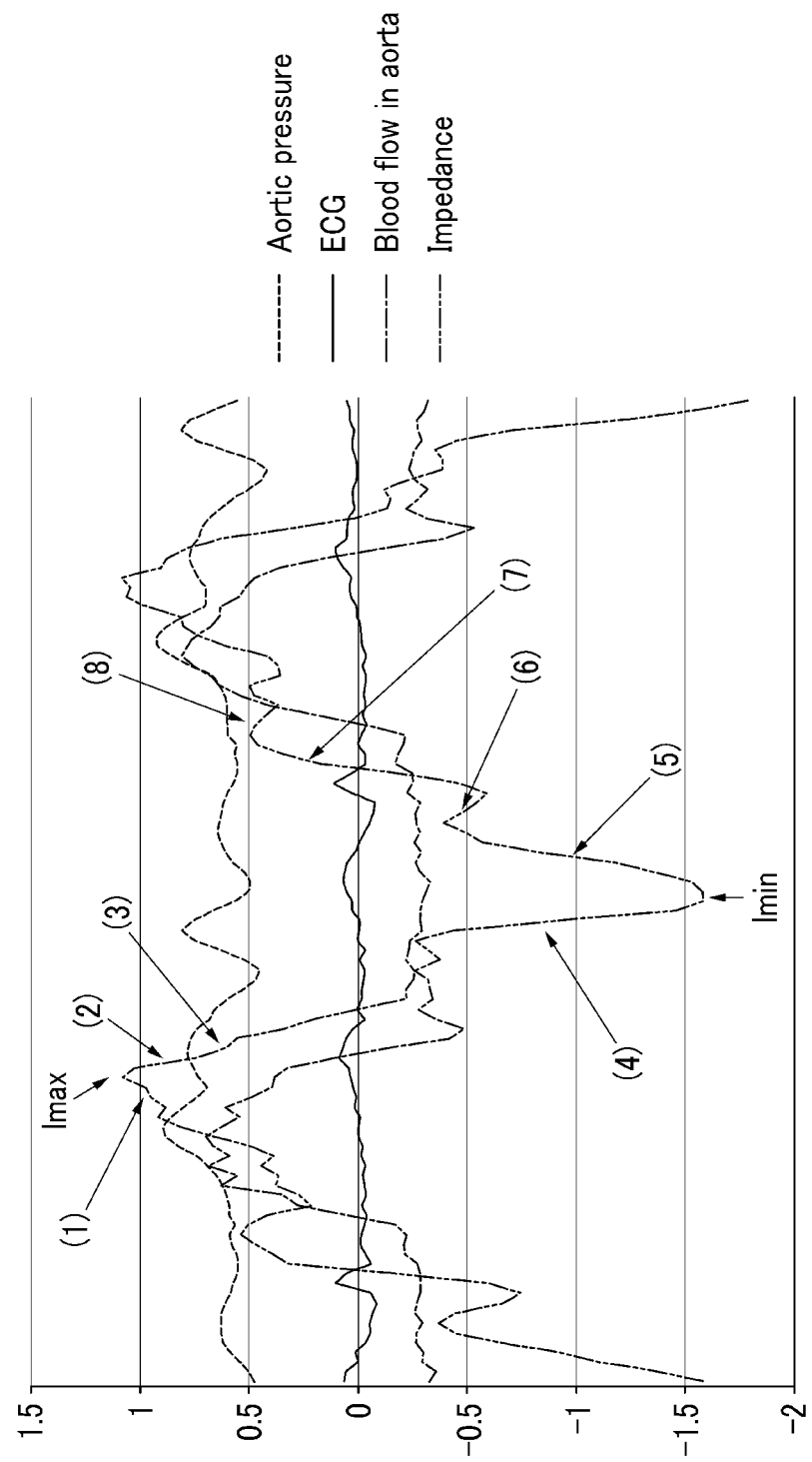
FIG. 14 is an enlarged view of a part of FIG. 13.
Figure 15:
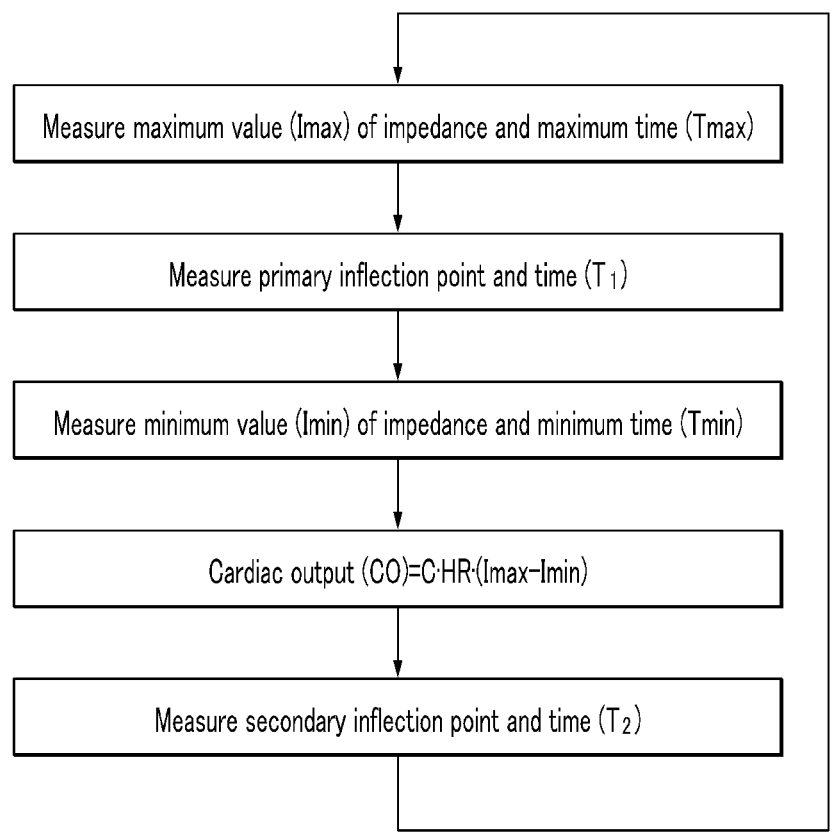
FIG. 15 is a flowchart illustrating steps of measuring an open and close timing of cardiac valves and a cardiac output through a variation in an impedance value.

FIG. 14 is an enlarged view of a part of FIG. 13. In Period 1, impedance increases due to ventricular systole and in Period 2, the impedance decreases due to expansion of artery. In Period 3, a slope in which the impedance decreases due to the close of an aortic valve is changed. In Period 4, the impedance decreases due to expansion of the ventricle and in Period 5, the expansion of the ventricle stops and the blood vessel is contracted, such that the impedance increases after passing the minimum value. In Period 6, the impedance decreases due to atrial systole, an additional expansion of the ventricle, and a temporary open of the aortic valve and in Period 7, the aortic valve is closed and the aorta is contracted, such that the impedance increases. In Period 8, the impedance decreases due to the open of the aortic valve. As described above, the impedance value is changed according to an open and close timing of the cardiac valves and contraction and expansion of the heart. Accordingly, the open and close timing of the cardiac valves and the cardiac output may be measured through the variation in the impedance value. FIG. 15 is a flowchart illustrating steps of measuring an open and close timing of cardiac valves and a cardiac output through a variation in an impedance value.

Referring to FIG. 15, an example of calculating the open and close timing of cardiac valves and the cardiac output by measuring the impedance will be described.

First, a maximum value $I_{max}$ of impedance I and a time $T_{max}$ are measured. The maximum value $I_{max}$ of impedance I is measured when the ventricle is maximally contracted. Next, inflection points and a time $T_1$ are measured by differentiating the impedance I. The inflection point between the maximum value $I_{max}$ and a minimum value $I_{min}$ of impedance I is generated by the close of the cardiac valves. Next, the minimum value $I_{min}$ and a time $T_{imm}$ of the impedance are measured. The minimum value $I_{min}$ of impedance I is measured when the ventricle is maximally expanded. Next, inflection points and a time $T_2$ are measured again by differentiating the impedance I. The inflection points after the minimum value $I_{min}$ are generated by the open of the cardiac valves.

The cardiac output CO may be calculated by multiplying an appropriate proportional constant C and a value obtained by multiplying a difference between the maximum value $I_{max}$ and minimum value $I_{min}$ of the impedance I by heart rate HR. The heart rate HR may be measured by an interval between the open time $T_2$ and the close time $T_1$ of the cardiac valves or an interval between a time $T_{max}$ reaching the maximum value of the impedance and a time $T_{min}$ reaching the minimum value of the impedance.

The control device 4 processes the signal measured by the impedance measuring device 6 through the microcontroller and controls the blood pump 3.

Figure 16:
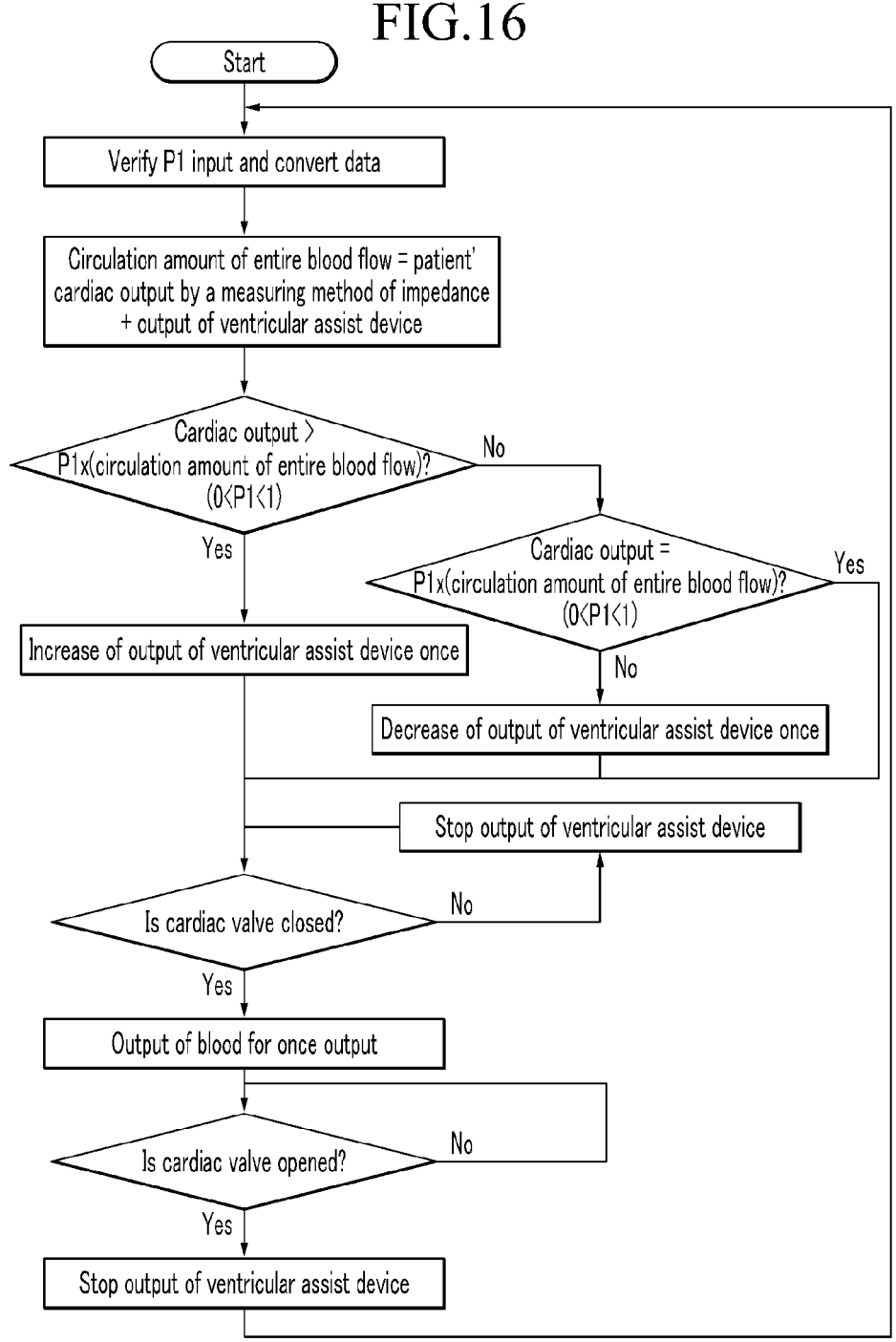
FIG. 16 is a flowchart illustrating steps of controlling a ventricular assist device by using an open and close timing of cardiac valves and a cardiac output measured value.

FIG. 16 is a flowchart illustrating steps of controlling a ventricular assist device by using an open and close timing of cardiac valves and a cardiac output measured value.

As shown in FIG. 16, the ventricular assist device may be controlled by comparing a cardiac output and a value obtained by multiplying a circulation amount of the entire blood flow by an input constant P1 and considering the open and close timing of cardiac valves. That is, the control device reduces the blood flow speed of the ventricular assist device when the circulation of the entire blood flow is reduced, such that the blood vessel is prevented from being contracted or damaged due to an excessive inflow of the blood flow. In addition, the control device may optimally control the blood pump 3 by a method of minimizing a load applied to the heart of the patient by preventing the blood ejection of the ventricular assist device in the heart ejection.

Figure 17:
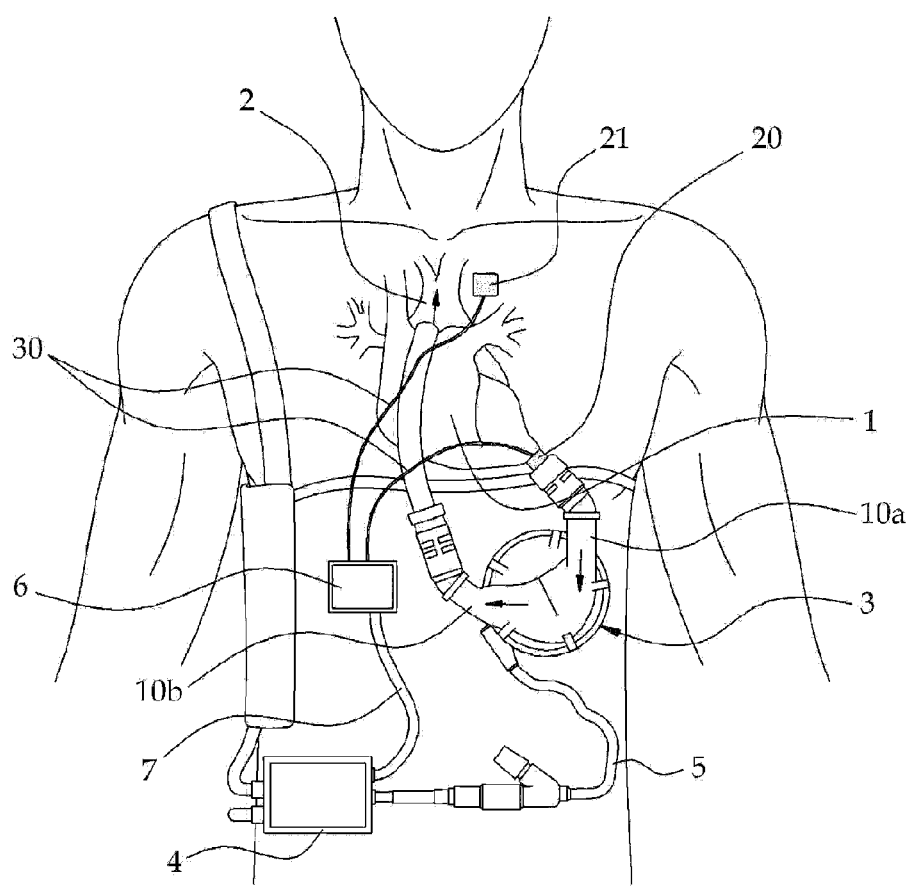
FIGS. 17 and 18 are diagrams illustrating a state where electrodes are installed in a ventricular assist device including an apparatus of measuring impedance according to other exemplary embodiments of the present invention.
Figure 18:
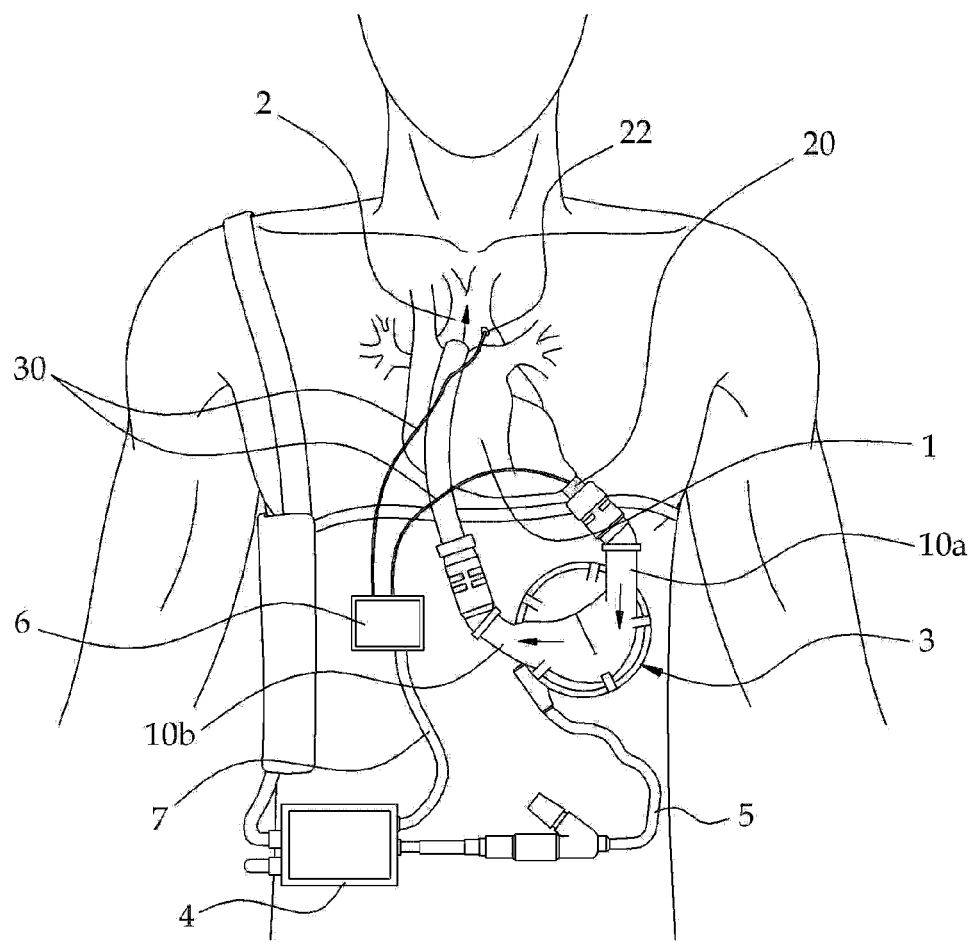

FIGS. 17 and 18 are diagrams illustrating a state where electrodes are installed according to other exemplary embodiments of the present invention.

As shown in FIGS. 17 and 18, instead of installing electrodes at the outflow conduit, an electrode 22 may be attached to the outside of the body around arteries and an implantable electrode 22 may be installed around the arteries inside the body.

Figure 19:
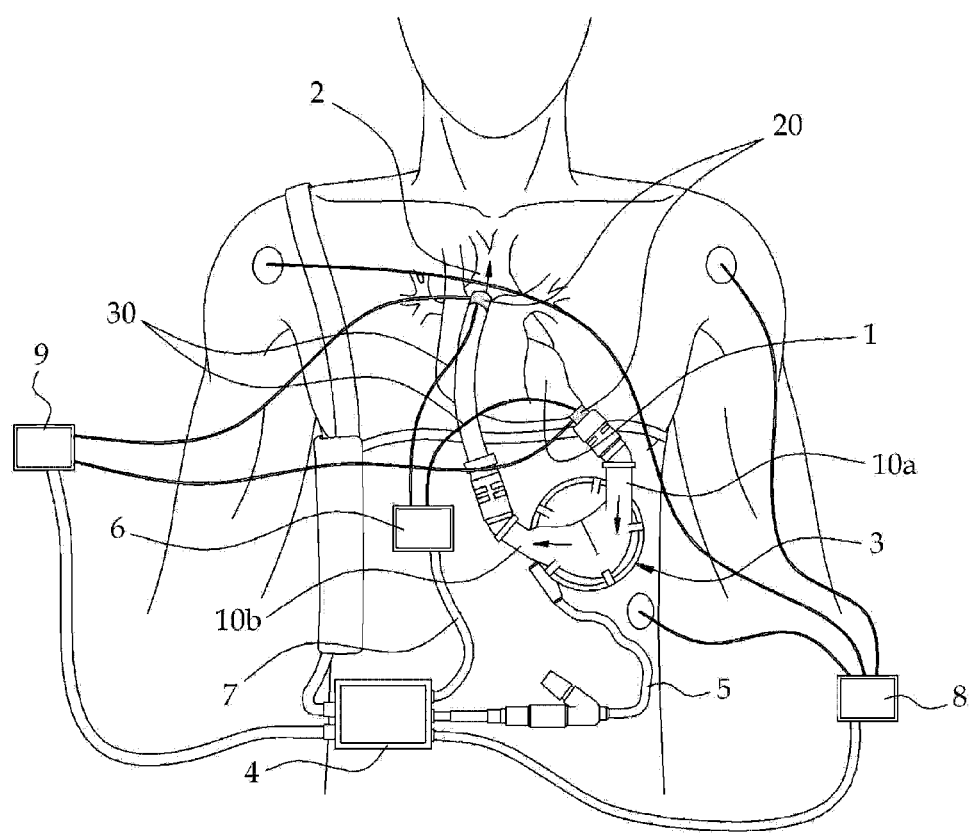
FIG. 19 is a conceptual view of a ventricular assist device including an artificial pacemaker according to an exemplary embodiment of the present invention.
Figure 20:
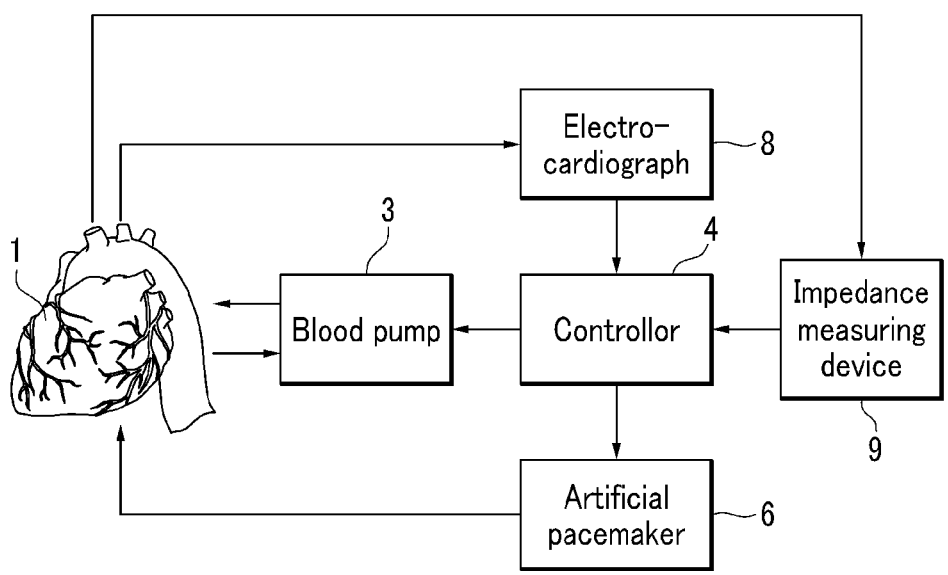
FIG. 20 is a block diagram of the ventricular assist device shown in FIG. 19.

FIG. 19 is a conceptual view of a ventricular assist device including an artificial pacemaker according to an exemplary embodiment of the present invention and FIG. 20 is a block diagram of the ventricular assist device shown in FIG. 19.

Referring to FIGS. 19 and 20, like a general ventricular assist device, a ventricular assist device including an artificial pacemaker according to an exemplary embodiment of the present invention includes inflow conduits 10a and 20 into which the blood in a ventricle 1 flows while being connected to the ventricle 1, a blood pump 3 connected to the inflow conduits 10a and 20 and pumping the blood, and outflow conduits 10b and 20 connecting the blood pump 3 and arteries 2 to transfer the blood ejected from the blood pump 3 to the arteries 2. The inflow conduits and the outflow conduits are hollow elongated pipes so that the blood can flow. The inflow conduits and the outflow conduits may be the ventricular assist device cannula shown in FIGS. 1 to 6.

The blood pump 3 may be classified into a pneumatic type and an electric type. The electric type is subdivided into an electrohydraulic type and an electromechanical type. The blood pump 3 stores the blood flowing from the inflow connecting tube 10a and includes a blood bag flowing out to the outflow connecting tube 10b, air allowing the blood to flow by expanding and compressing the blood bag, and an electric device. Since the blood pump 3 uses a known device, the detailed description thereof is omitted.

Referring to FIGS. 19 and 20, the ventricular assist device including an artificial pacemaker according to the exemplary embodiment of the present invention further includes detecting devices 8 and 9 detecting cardiac signals such as heart rate, a QRS generating time, a cardiac output, an open and close timing of cardiac valves, and the like, an artificial pacemaker 6 applying an electric stimulus to the heart through the electrode 20 of the conduit, and a control device 4 controlling the blood pump 3 and the artificial pacemaker 6 by receiving the signal from the detecting devices 8 and 9.

The detecting device includes an electrocardiograph 8. The electrocardiogram records active current according to contraction of the heart in a curve line and is abbreviated to ECG or EKG. Since excitement of the heart muscle is generated from a venous sinus to proceed in atrium and ventricle directions, when the excitement is induced to the electrocardiograph in two arbitrary points, the active current of the heart is drawn as a graph. As described above, the electrocardiogram is acquired. A contracted state or a relaxed state of the heart may be determined through the electrocardiogram.

Further, the detecting device further includes an impedance measuring device 9 measuring the impedance between the electrodes 20 of the inflow conduit and the outflow conduit. As the high-frequency current generated from the power supply device of the impedance measuring device 9 passes the heart and the blood vessel through the electrodes, high-frequency voltage is generated in proportion to magnitudes of impedances of the heart and the blood vessel. The impedance measuring device 9 measures variation in an impedance value by measuring and recording the high-frequency voltage generated by the change of the impedance due to the heart beat. The impedance value is changed according to open and close of cardiac valves, blood flow in ventricles, and blood flow in aorta, such that an open and close timing of the cardiac valves and variation in blood flow may be measured by using the variation in the impedance value.

The artificial pacemaker 6 is implanted in the upper side of a chest with being not seen at the outside or implanted together with being included in the control device 4. The artificial pacemaker 6 includes a battery power management circuit for transferring the stimulus to the heart, a voltage/current reference oscillator, a high voltage multiplier, a high voltage output pulse generator, and the like. In addition, the power can be supplied through the ventricular assist device during the charging or in emergency. Since the artificial pacemaker 6 uses a known device, the detailed description thereof is omitted.

The control device 4 includes an integrated circuit which processes the signals measured through the detecting devices 8 and 9, monitors the variations in a heart beat speed, an open and close timing of the cardiac valves, and the variation in the blood flow, supplies the stimulus by controlling the artificial pacemaker 6 if necessary, and can control the blood flow ejected through the ventricular assist device by controlling the blood pump 3.

Figure 21:
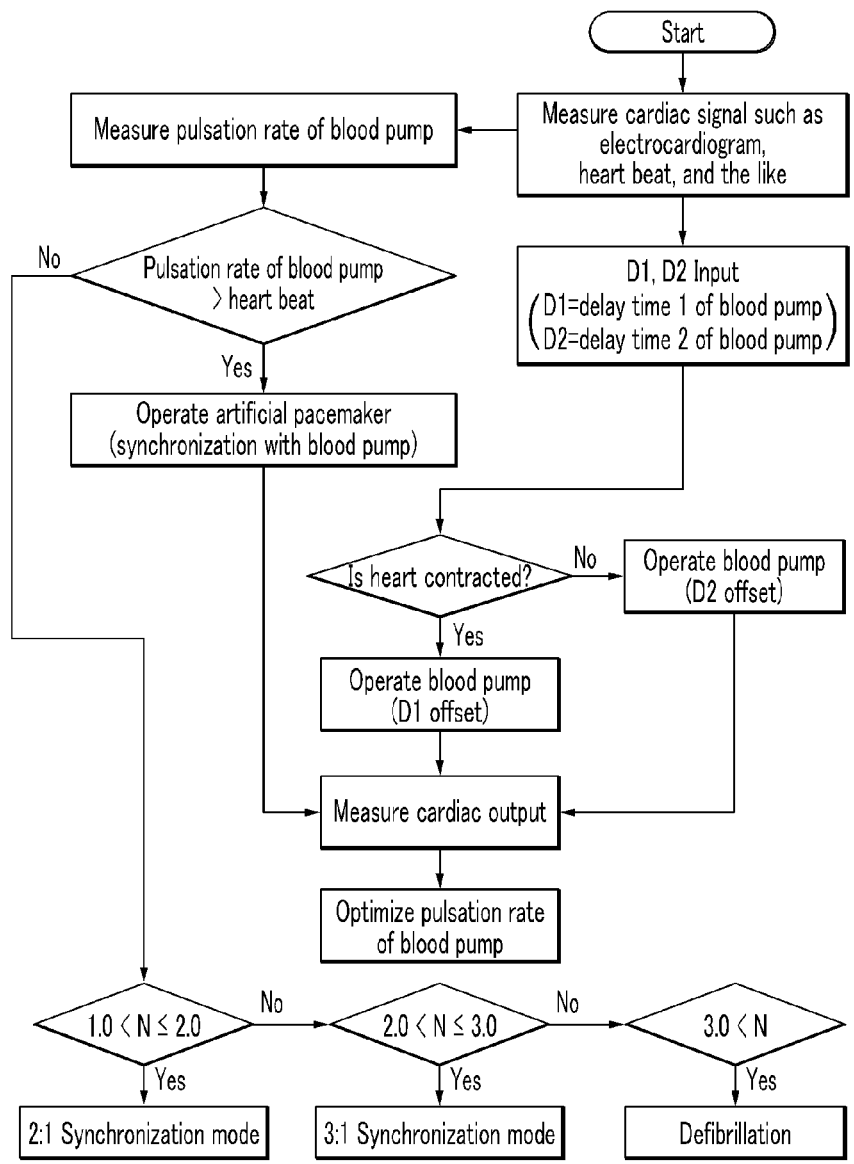
FIG. 21 is a flowchart illustrating operational steps of the ventricular assist device shown in FIG. 19.

FIG. 21 is a flowchart illustrating operational steps of the ventricular assist device shown in FIG. 19.

Referring to FIG. 21, operational steps of a ventricular assist device including an artificial pacemaker according to an exemplary embodiment of the present invention start from measuring a cardiac state through a detecting device. Whether the heart of patient is in the contracted state or the relaxed state is determined by analyzing a cardiac signal and the blood pump operates after delay times D1 and D2 inputted according to the cardiac state elapse. In this case, an output by the blood pump is optimized by using the cardiac output calculated by measuring the impedance of the heart. In the case where the heart rate is lower than pulsation rate of the blood pump, the heart rate is controlled so as to be equal to the pulsation rate of the blood pump by applying the stimulus to the heart through the artificial pacemaker. In the case where the heart rate is one to two times higher than pulsation rate of the blood pump, the heart rate is controlled so as to be two times higher than the pulsation rate of the blood pump by applying the stimulus to the heart through the artificial pacemaker. That is, when the patient's heart pulsates twice, the blood pump pulsates once. In the case where the heart rate is two to three times higher than pulsation rate of the blood pump, the heart rate is controlled so as to be three times higher than the pulsation rate of the blood pump by applying the stimulus to the heart through the artificial pacemaker. That is, when the patient's heart pulsates three times, the blood pump pulsates once.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A ventricular assist device including a blood pump pumping blood, comprising:
    a first conduit including a first connecting tube connecting an incision of a first body tissue and the blood pump so that the blood can flow, and a first electrode connected to an end portion of the first connecting tube and contacting the incision of the first body tissue to transfer an electric signal to the first body tissue;
    a second conduit including a second connecting tube connecting an incision of a second body tissue and the blood pump so that the blood can flow, and a second electrode connected to an end portion of the second connecting tube and contacting the incision of the second body tissue to transfer another electric signal to the second body tissue, the second electrode being spaced apart from the first electrode;
    an impedance measuring device measuring impedance between the first electrode and the second electrode;
    a control device receiving a signal from the impedance measuring device to control operation of the blood pump.

2. The ventricular assist device including an impedance measuring device of claim 1, wherein:
    the second electrode is
    an electrode patch attached to the skin.

3. The ventricular assist device including an impedance measuring device of claim 1, wherein:
    the second electrode is
    an implantable electrode installed in the body.

4. The ventricular assist device including an impedance measuring device of claim 1, wherein:
    the first electrode is
    a conductive sheet attached to the surface of the connecting tube.

5. The ventricular assist device including an impedance measuring device of claim 1, wherein:
    the first electrode is
    a hollow electrode having a hollow space where the connecting tube is inserted at the inside thereof and contacted to the incision of the first body tissue at the outside thereof.

6. The ventricular assist device including an impedance measuring device of claim 5, wherein:
   a receiving groove receiving the incision of the first body tissue is formed at an outer circumference of the hollow electrode.

7. The ventricular assist device including an impedance measuring device of claim 1, wherein:
   the first electrode is
   a connector electrode which has a hollow space where the blood can flow at the inside thereof and includes a body part contacted to the incision of the first body tissue and inserted into the first body tissue and a fixing part extending from the body part and inserted and fixed to the connecting tube at the outside thereof.

8. The ventricular assist device including an impedance measuring device of claim 7, wherein:
   a receiving groove receiving the incision of the first body tissue is formed at an outer circumference of the body part.

9. The ventricular assist device including an impedance measuring device of claim 1, wherein:
   the first electrode
   has hollow space where the blood can flow at the inside thereof and includes a body part contacted to the incision of the first body tissue and fixing parts extending from the body part to the upstream and the downstream, respectively, at the outside thereof, and
   the connecting tube includes
   a first connecting tube having one end connected to the fixing part and the other end inserted into the first body tissue and a second connecting tube having one end connected to the fixing part and the other end connected to the ventricular assist device.

10. The ventricular assist device including an impedance measuring device of claim 9, wherein:
    a receiving groove receiving the incision of the first body tissue is formed at an outer circumference of the body part.

* * * * *